US011559199B2

United States Patent
Mayer et al.

(10) Patent No.: US 11,559,199 B2
(45) Date of Patent: Jan. 24, 2023

(54) VISUAL CONTRAST SENSITIVITY CARDS FOR PEDIATRIC SUBJECTS

(71) Applicant: New England College of Optometry, Boston, MA (US)

(72) Inventors: Dale Luisa Mayer, Brookline, MA (US); Barry S. Kran, Southborough, MA (US)

(73) Assignee: New England College of Optometry, Boston, MA (US)

( * ) Notice: Subject to any disclaimer, the term of this patent is extended or adjusted under 35 U.S.C. 154(b) by 312 days.

(21) Appl. No.: 16/943,285

(22) Filed: Jul. 30, 2020

(65) Prior Publication Data
US 2022/0031157 A1 Feb. 3, 2022

(51) Int. Cl.
*A61B 3/02* (2006.01)
*A61B 3/032* (2006.01)

(52) U.S. Cl.
CPC .............. *A61B 3/022* (2013.01); *A61B 3/032* (2013.01); *A61B 2503/04* (2013.01); *A61B 2503/06* (2013.01)

(58) Field of Classification Search
CPC ..... A61B 3/022; A61B 3/032; A61B 2503/06; A61B 3/0041; A61B 3/0058
USPC .................... D21/376, 383, 384; D19/59, 60
See application file for complete search history.

(56) References Cited

U.S. PATENT DOCUMENTS

2007/0048693 A1* 3/2007 Hannan ................... G09B 1/04
434/156
2011/0085140 A1* 4/2011 Brown .................. A61B 3/028
351/239

OTHER PUBLICATIONS

"Development of Form Visual Acuity in Infants Measured by Schematic Faces" Thesis, Norah Alkanhal, 2018.*
Chong & Mohamed, New Paediatric Contrast Test: Hiding Heidi Low-contrast 'face' test, Clinical and Experimental Opbtbalmology, No. 31, pp. 430-434, 2003.
Elgohary et al., "Age Norms for Grating Acuity and Contrast Sensitivity Measured by Lea Tests in the First Three Years of Life", Int. J. Ophthalmol, vol. 10, No. 7. Jul. 18, 2017.
Hopkins et al. The Ohio Contrast Cards: Visual Performance in a Pediatric Low-vision Site, Optom Vis Sci. vol. 94, No. 10, 2017, www.optvissci.com.

* cited by examiner

*Primary Examiner* — Jordan M Schwartz
(74) *Attorney, Agent, or Firm* — Norris McLaughlin, P.A.

(57) ABSTRACT

A visual stimulus for a set of contrast cards is provided which comprises a hollow outer circle, opposing and identical first and second arc segment within the outer circle which are symmetrical about the vertical diameter of the outer circle, a first filled-in circle and a second filled-in circle being identical in diameter to the first filled-in circle, each residing on opposite ends of the horizontal diameter of the outer circle and each being equidistant from the center of the outer circle, a filled-in center element having a rotational center on the center of the outer circle, the center element being symmetrical about both the horizontal and vertical diameter of the outer circle.

12 Claims, 6 Drawing Sheets

VISUAL CONTRAST SENSITIVITY CARDS FOR PEDIATRIC SUBJECTS

BACKGROUND OF THE INVENTION

Field of the Invention

The invention relates to a set of contrast cards for assessing contrast sensitivity (CS) for pediatric subjects diagnosed with ocular disorders or cerebral visual impairment (CVI). Contrast sensitivity (CS) loss is associated with impaired daily living skills in adults including difficulties in mobility, driving, face recognition, using tools, and finding objects. CS may be a better predictor of performance in activities such as discriminating between objects, recognizing faces, and judging distance than visual acuity (VA). Thus, there is good reason to measure both CS and VA in individuals with visual impairments; both need to be considered when managing habilitation and rehabilitation

Discussion of the Prior Art

Recent studies report that functional visual abilities and vision-related quality of life (QoL) are reduced in children with congenital ocular disorders. An extensive study of diverse pediatric vision disorders found impaired functional vision and eye-related QoL in children with moderate-severe visual impairment defined by their visual acuity deficit. A study of adolescents with low vision tested with the Ohio Contrast Cards (OCC) found that CS correlated with vision-related Quality of life (QoL), while visual acuity did not. This study provides some evidence that CS may be more sensitive than VA to aspects of vision-related QoL.

Efficient and reliable tests of letter CS are in widespread clinical use. Other clinical tests measure the contrast sensitivity function (CSF) using sine-wave gratings. However, letter identification and grating orientation skills tend to not be reliable under age 4 to 5 years. Visual evoked potentials (VEP) can measure the contrast sensitivity of children with ocular and neurological disorders, including cortical vision impairment (CVI). However, VEPs do not measure behavior, rather the physiological response of the visual pathway. Clinical use of VEP tends to be restricted to specialized practices because complex equipment, specialized procedures, and experienced personnel are required.

Behavioral tests developed to assess CS in infants and children are more straightforward to administer in the clinic because the examiner directly assesses the child's "looking" response. Pediatric CS test stimuli include sine-wave gratings (Contrast Sensitivity Card Test, CSCT), a large low frequency square wave grating (Ohio Contrast Cards, OCC), schematic face stimuli (Hiding Heidi, HH, www.good-lite.com; Mr. Happy), and picture outlines (Cardiff Contrast Test, CCT, www.eyesfirst.eu). There are limitations to these tests and their clinical applications. For example, measuring a CSF with sine-wave gratings (CSCT) is time-consuming and requires two people. Other tests have a relatively low maximum CS (e.g., HH, Mr. Happy, CCT) and their test-retest reliability has not been reported. Nor have most tests been validated against a standard CS test. Finally, clinical feasibility has not been determined for young patients with visual and multiple impairments.

Further, in card sets having a centered image, such as HH (Chen A H, Mohamed D. New paediatric contrast test: Hiding Heidi low-contrast 'face' 492 test. *Clin Exp Ophthal.* 2003; 31:430-4. 493; Elgohary A A, Abuelela M H, Eldin A A. Age norms for grating acuity and contrast 494 sensitivity measured by Lea tests in the first three years of life. *Int J Ophthalmol.* 495 2017; 10:1150-3) shown in FIG. 2A, and the test protocol calls for the tester to present two cards to the subject, one with the HH face and other with a blank gray card. Because HH stimuli of different contrasts are printed on both sides of a test card, the examiner will be aware of which of the two have the HH face. This makes the HH test susceptible to examiner bias. Pediatric vision tests that employ a two alternative, forced choice (2AFC) paradigm where the same stimulus can appear on either the child's right or left, and where the task of the examiner is to judge whether the stimulus is on the child's left or right, have greater protection against examiner bias than the HH test. A 2AFC procedure requires that the test stimulus is identical in either right or left position and this is not possible with the HH face; it is not symmetrical around the horizontal and vertical axes. Another factor affecting the HH test is distractibility and consequent variable performance of the child who may focus on the examiner's face between the two HH test cards. Furthermore, the HH stimulus is created by variable spatial frequencies producing features that vary in size and width. This means the HH stimulus cannot be specified by its underlying spatial frequency (SF) channel and thus its location along the SF axis of the CSF cannot be defined. This may result in insensitivity to many visual disorders. (The CSF describes low to high resolution of visual stimuli and is underpinned by multiple SF channels, with peak sensitivities at correspondingly low to high SFs.) For the prior art card set of HH stimuli shown in FIG. 2B, it can be seen that the stimulus images extend nearly to the edge of the card, which may result in the examiner's fingers covering a portion of the HH face.

The new OCC CS test (Hopkins G R, Doherty B E, Brown A M. The Ohio Contrast Cards: Visual performance in a pediatric low-vision site. *Optom Vis Sci.* 2017; 94:946-56) uses a stimulus consisting of a very low spatial frequency (large black and white bars) square-wave grating (two examples are shown in FIG. 2B) which is printed displaced from the center of the front of the large test card. This enables testing CS using a 2AFC procedure because the grating stimulus, although not exactly symmetrical along the horizontal axis it is symmetrical on the vertical axis and it is the same 3 cycle grating where ever it is presented to the subject's gaze. The card has a central viewing hole through which the examiner views the child. Because the examiner holds the card with the stimulus side toward the subject, the examiner does not know the location of the grating and thus can be relatively unbiased. The grating bars are the same width across the stimulus. This means the OCC grating stimulus can be defined in terms of its channel SF and thus has a specific location on the SF axis of the CSF. The OCC stimulus, 22 cm×20 cm, fills a large part of a subject's field and thus is a very distinctive and salient stimulus. However, it may not have the intrinsic interest to pediatric subjects as a 'face' stimulus.

SUMMARY OF THE INVENTION

The inventors have developed a stimulus and test procedure to address the limitations of previously developed pediatric tests of CS. First, the stimulus is a schematic representation of a 'face' in order to attract the attention of pediatric subjects. The stimulus has been designated as the "Double Happy" ("DH") stimulus. The face features have a relatively constant width and the spaces between the elements are also relatively constant. This allows the face features to be defined approximately in terms of a single SF.

The face stimulus can also be defined in terms of a channel SF by calculating the number of strokes across the stimulus visual angle. Both the feature SF and the channel SF are localized on the SF axis of the CSF at the low frequency portion. The face stimulus can thereby be described in relation to the CSF and in relation to the subject's visual acuity (high frequency end of CSF).

The face stimulus is offset from the center of a rectangular card. When the card is rotated 180 deg, as is done routinely in testing to present the face on the right and left of the patient's gaze, the face is identical in form. This due to the symmetry of the design of the face around its horizontal and vertical axes. (The symmetrical appearance of the face when the card is rotated 180 deg enables testing using 2AFC procedure.)

The examiner holds the test card central to the child's gaze direction and can view the child's face through a small central hole. The examiner is unaware of the location of the face stimulus while testing a contrast card because the rear of the card contains no information on the face location. This allows the examiner to maintain objectivity until s/he can judge whether the child detects the face contrast.

Furthermore, in contrast to prior art HH facial representation (FIG. 2A), the present invention presents an abstract face which arguably may be perceived as more "neutral" in terms of cultural associations than HH.

The face stimulus is preferably smaller in overall size than the OCC grating (12 cm vs. 20×22 cm) which may make it easier for the examiner to judge the right/left location of the face as the child fixates it compared to the extended OCC grating.

Feasibility, test-retest reliability, and inter-examiner reliability of this new CS test were assessed in a clinical population of children diagnosed with ocular disorders or cortical/cerebral visual impairment (CVI). CS results were analyzed by age, visual acuity, and diagnosis.

The inventors have designed a novel schematic smiling face stimulus that would appeal to young children, which has been designated as the Double Happy (DH) face stimulus (as shown in FIG. 1). While multiple spatial frequencies comprise the HH face (shown in FIG. 2B), the features in the DH face are constrained to a narrow band of spatial frequencies enabling the testing of a restricted range of spatial frequencies. The DH stimulus is offset from the center of a card which is preferably 40 cm wide by 25 cm high cards, whereas the HH faces fill the entire test card. The DH face stimulus is identical when rotated by 180 degrees (FIG. 1). This characteristic led to the name, Double Happy Contrast Sensitivity Test, abbreviated DH CS test. Each stimulus should preferably occupy a space which is horizontally centered within one half of the card (defined by an imaginary line running vertically through the horizontal center of the card), and preferably vertically centered as well.

In particular, provided herein is a visual stimulus for a set of contrast cards, the stimulus comprising:

A hollow outer circle having a constant thickness,

Two "smiles" defined by a first arc segment within the outer circle which is symmetrical about the vertical diameter of the outer circle, and a second arc segment in opposing arrangement to the first arc segment and being identical in length and thickness to the first arc segment, the second arc segment being symmetrical about the vertical axis of the outer circle, the first and second arc segments being located on an imaginary circle residing within the outer circle and being concentric therewith, Two "eyes" defined by a first filled-in circle and a second filled-in circle being identical in diameter to the first filled-in circle, each residing on opposite ends of the horizontal diameter of the outer circle and each being equidistant from the center of the outer circle, and A "nose" defined by a filled-in center element having a rotational center on the center of the outer circle, the center element being symmetrical about both the horizontal and vertical diameter of the outer circle.

In various preferred embodiments, one or more of the following parameters may be applicable:

the thickness of the first and second arc segments is substantially the same as the thickness of the outer circle;

the length of the first and second arc segments are each from about 80 to 100 degrees of a circle, preferably about 90 degrees;

each of the lateral ends of each of the first and second arc segments are rounded;

each of the first and second filled-in circle have a diameter which is substantially equal to the thickness of the outer circle;

the center element has a horizontal width which is substantially equal to the thickness of the outer circle; and is preferably a vertically oriented ellipse;

the radial distance between an inner concave edge of the outer circle and a convex outer edge of the first arc segment is substantially equal to the thickness of the outer circle.

The visual stimulus image is present on a set of contrast cards, which is a plurality of identically sized rectangular cards, each having on at least one side thereof the visual stimulus image of the invention. The stimulus image is located at an identical location on each of the cards, the location being wholly within one lateral half of the card and centered on the horizontal bisecting line. Preferably, the location of the visual stimulus image is centered along a vertical line bisecting said one lateral half of the card, and each of the cards has a viewing hole located at the intersection of the horizontal bisecting line of the rectangle and a vertical bisecting line of the rectangle.

The cards are white, and the face stimulus is a darker, neutral gray color. The contrast of the face ranges from high—a black or dark face—to low—a dim gray. In a full 15 card set, the contrast will generally differ between adjacent cards in fixed intervals, according to parameters known in the field. However, the contrast difference between cards may be chosen to vary according to need; for example, in a smaller 'sample' set of cards, such as a 6 card set, the intervals may be chosen by the skilled person.

Figure 4:
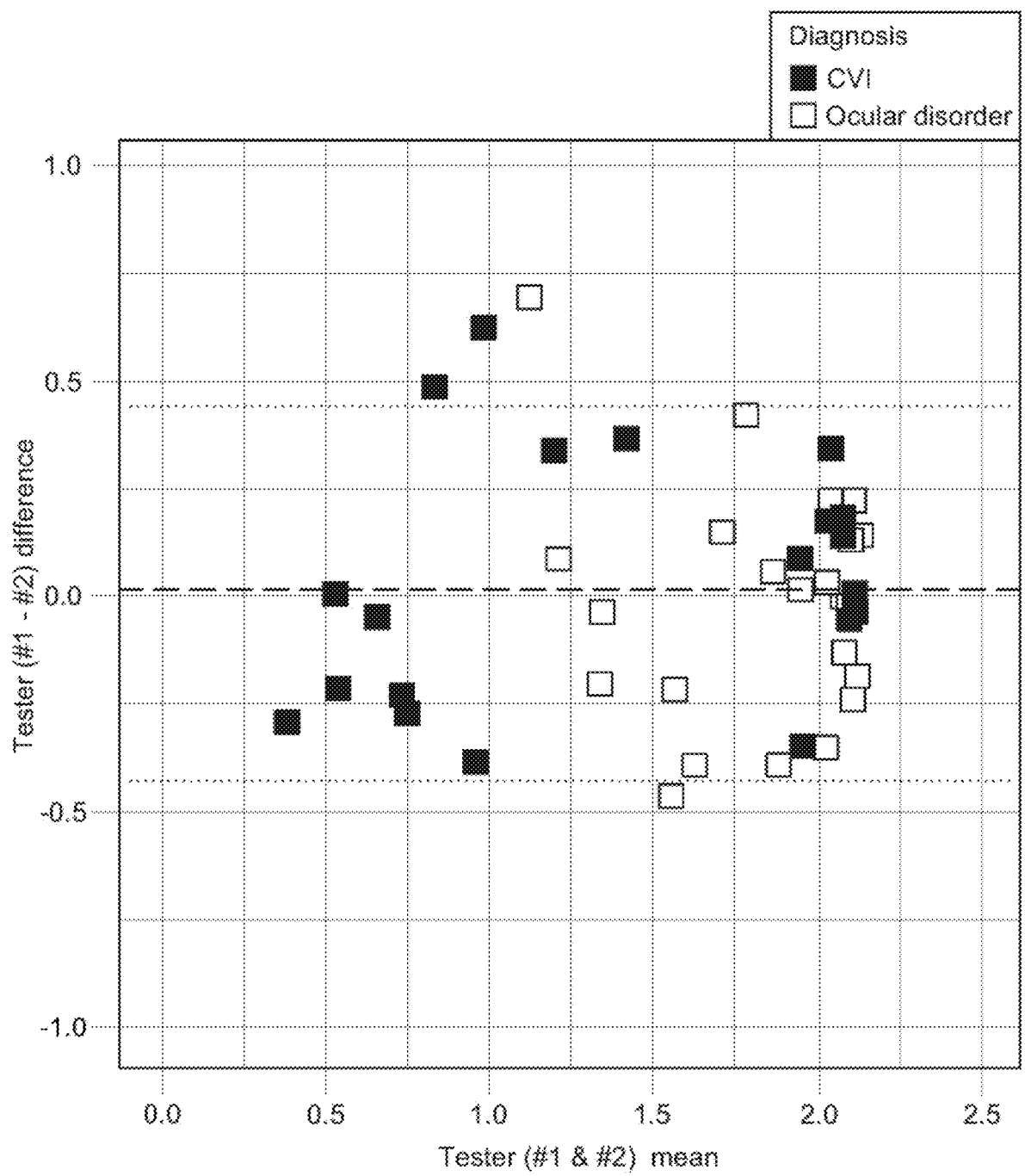

FIG. 4 shows a scatter diagram in which the filled squares represent DH $\log_{10}$ CS scores for the CVI patients and the open squares for those with ocular disorder. The abscissa is the mean of the scores from the two testers and the ordinate the difference. The dashed line is the median difference between the two testers, and the dotted lines the limits of the 95% confidence interval on the difference. Note that DH $\log_{10}$ CS scores were lower for those with CVI.

Figure 5:
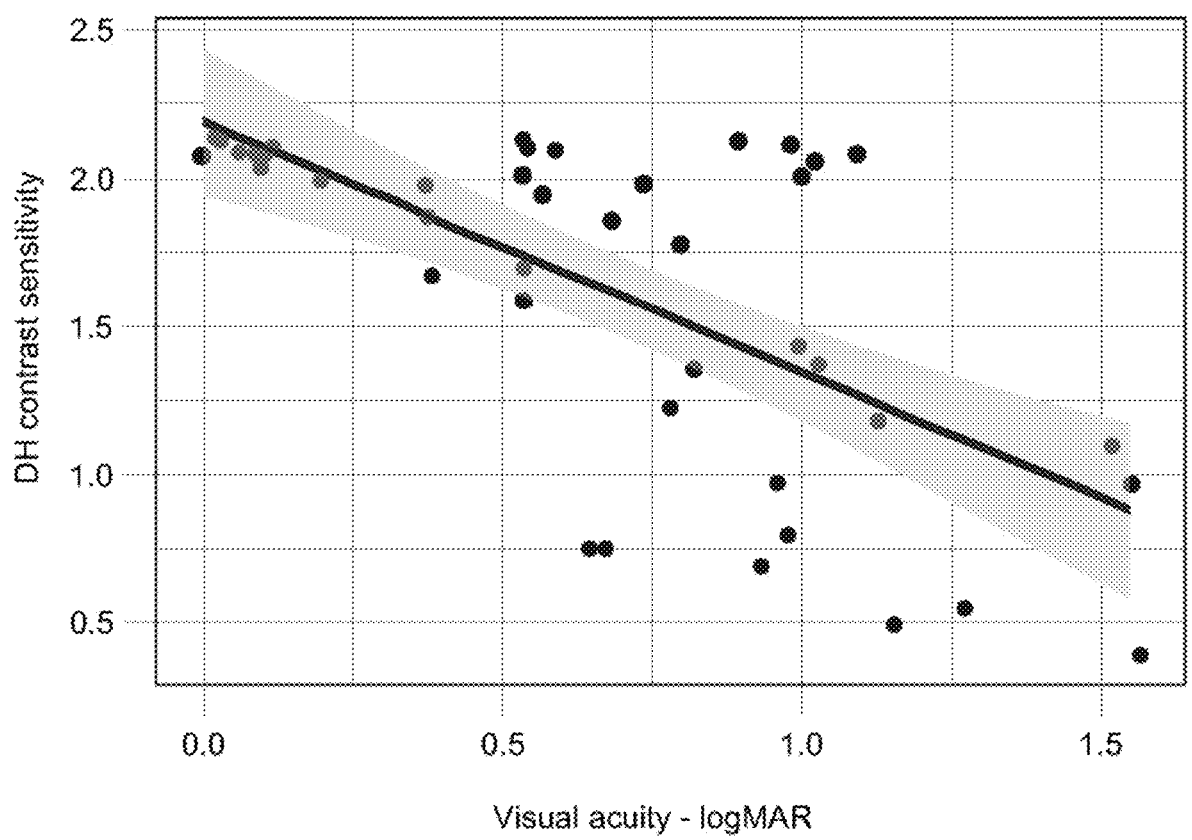

FIG. 5 shows a graph of visual acuity versus DH contrast sensitivity for all participants. The solid black line shows the line of best fit and the shaded region the 95% confidence interval. Note that DH $\log_{10}$ CS and VA were reduced in participants with CVI compared to those with ocular disorder.

DETAILED DESCRIPTION OF THE INVENTION

Figure 1A:
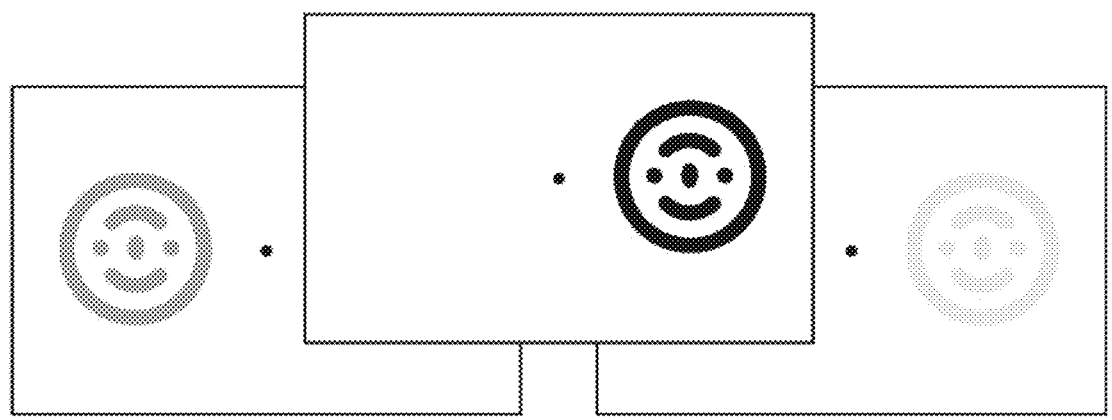
FIG. 1A shows a selection of three of the inventive stimulus image contrast test cards at different contrast levels: high contrast in the center, mid-level contrast on the left, and low contrast on the right.
Figure 1B:
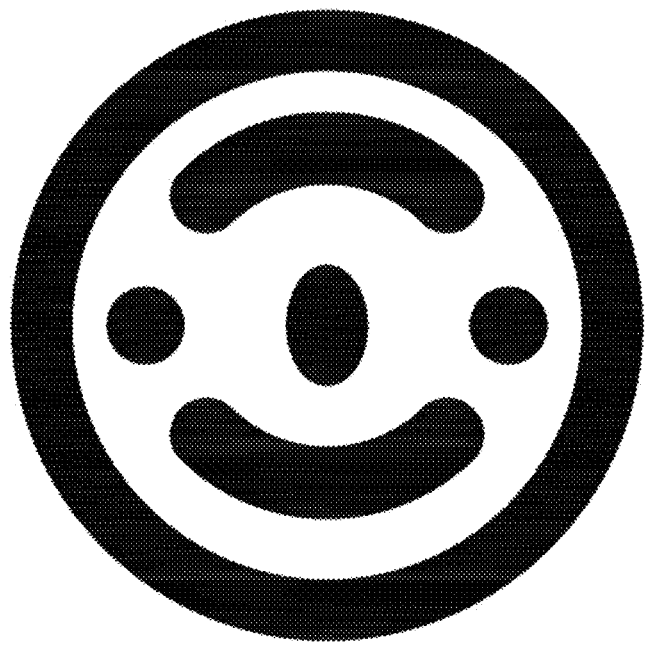
FIG. 1B shows the stimulus image of the invention.
Figure 1C:
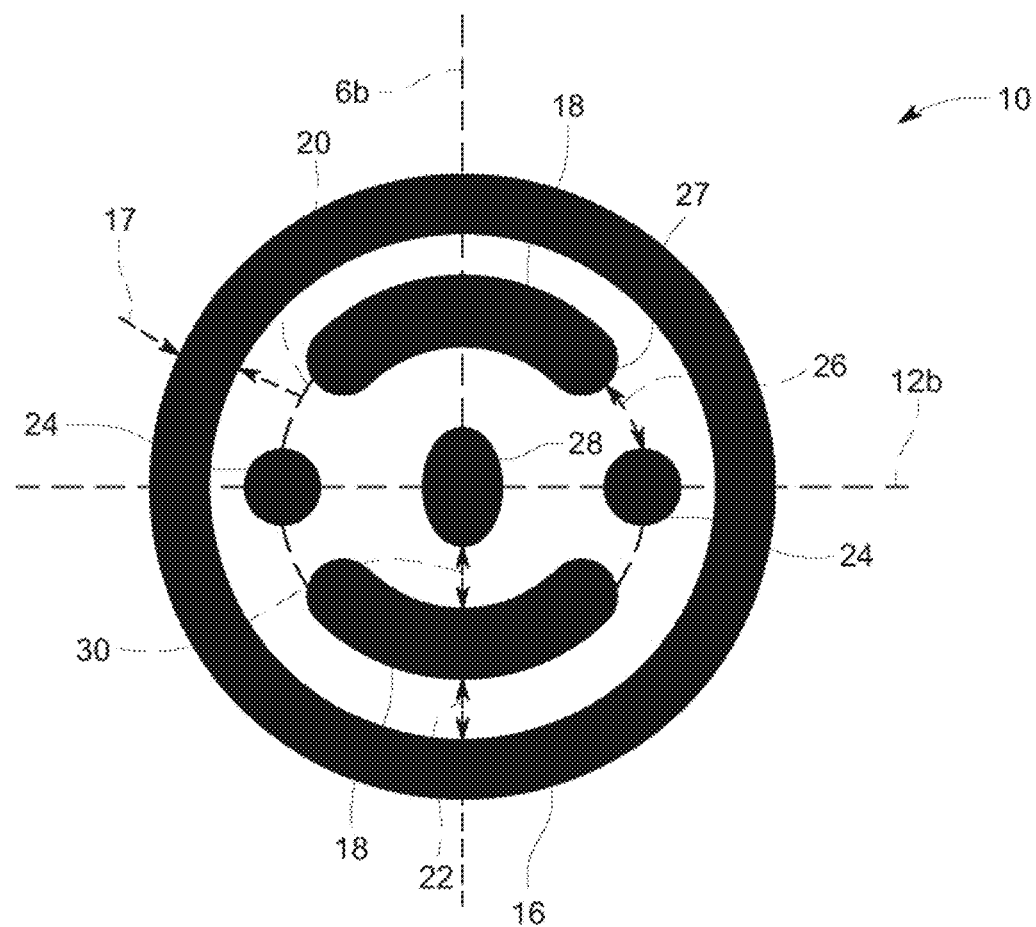
FIG. 1C shows the stimulus image of the invention.
Figure 1D:
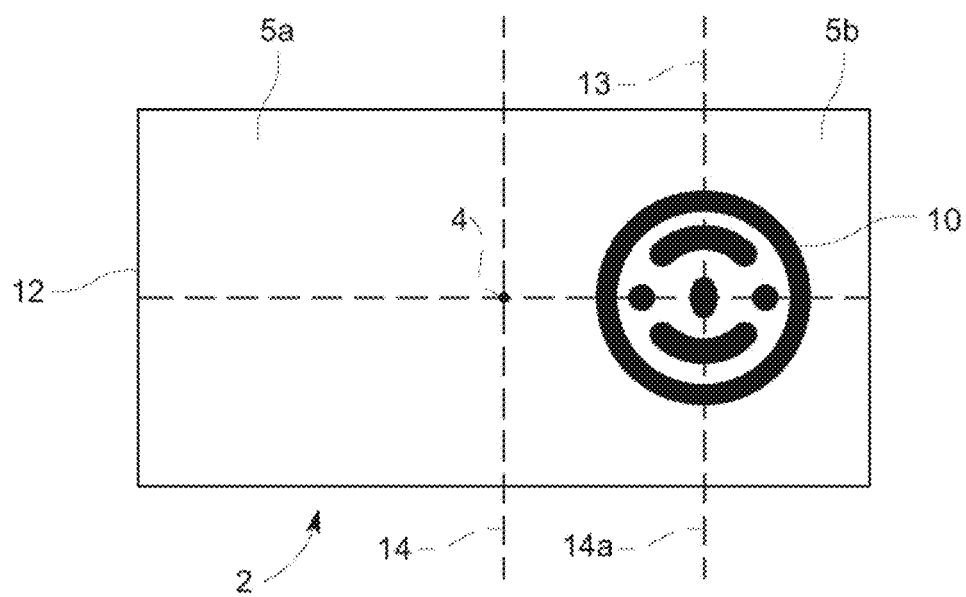
FIG. 1D shows a contrast card according to the invention.

The stimulus of the invention is as substantially shown in FIGS. 1B and 1C. While a selection of three cards 2 is shown in FIG. 1A for illustration purposes, it is preferable that the testing set of contrast cards comprises 15 cards ranging from low contrast to high contrast, and additionally one blank card. However, the number of cards in a set may be changed, and the contrast interval may vary according to the needs of a particular testing protocol. FIG. 1D is provided to show location and orientation of the stimulus on the card.

With reference to FIGS. 1C and 1D, a viewing hole 4 is preferably located at the horizontal center (i.e. at the intersection of the bisecting axes 12, 14), and is preferably vertically centered as well. With respect to a half of each card representing left and right halves 5a 5b, the stimulus 10 is preferably located in a horizontally centered orientation within one half (shown as 5b) so that a clear distinction can be seen between a left oriented and right oriented card, while keeping the stimulus sufficiently distant from the card edge. It is noted that the terms right and left are used only for purposes of the present description, as the cards themselves may be oriented in either direction about its horizontal axis. In this regard, it is seen that an important part of the inventive stimulus is that it be symmetrical about both the horizontal 12 and vertical 14a axes. Thus, the inventive stimulus is the same configuration in right/left or up/down orientations. This allows for a random orientation in the presentation of the card set to the test subject. Because the stimulus is on the front side of the card which the tester presents to the subject, the tester sees only the blank rear of the card, thus removing bias of the tester, as the tester does not know on which side the stimulus is while presenting it to the subject.

The stimulus 10 is in the form of an outer circle 16 having a particular constant thickness 17. Two identical but opposing 'smiles' are present in the form of an arc segment 18, one each within the upper and lower part of the space within the outer circle and each centered about a vertical diameter 6b running through the outer circle 16. The arcs 18 preferably have substantially the same thickness 17 as the circle and themselves reside along an imaginary inner circle 20 being concentric with the outer circle 16. Each arc segment 18 has a circumferential arc of about 80-100 degrees, and preferably about 90 degrees of a circle. Preferably, the space 22 between the outer convex edge of each arc is substantially the same as the thickness 17 of the circle and arc segments to provide a relatively consistent spatial frequency throughout the stimulus design 10.

Two 'eyes' 24 are present on either side of the vertical diameter 6b, spaced equally therefrom along a horizontal diameter 12b. Preferably the eyes are in the form of filled-in circles 24 having a diameter which is substantially equal to the thickness 17 of the outer circle, and preferably are located on the imaginary inner circle 20, more preferably with their centers on the inner circle 20. In a most preferred embodiment, the arc segments 18 have an arc length such that the distance 26 along the imaginary inner circle 20 (i.e. the space) between an end 27 of an arc segment and the outside of the eye 24 is substantially the thickness 17 of the outer circle. It is noted that the shape, thickness and distance from vertical center of the eyes may vary. For example, the eyes may be hollow circles, or shaped as horizontal ovals, and may be spaced within or without the inner circle. Likewise, the two smile arc segments may be of a thickness different form the outer circle. However, the preferred parameters set out above have the effect of maximizing spatial frequency and providing a pleasing, harmonious and visually stimulating design in which distracting elements have been minimized. In this regard, it may be considered that one preferable design of the stimulus has the thickness of the outer circle at about 20-25%, and more preferably about 22%, of the outside radius of the outer circle. In the present discussion, it should be understood that the term 'substantially' in terms of dimensions means within +/−10%, preferably +/−5% and more preferably +/−2%.

At the center of the stimulus image 10 is a vertically oriented 'nose' 28, preferably in the form of a filled-in vertical ellipse, the foci of which lie on the vertical diameter 6b of the outer circle 16, the ellipse 28 being centered about the horizontal diameter 12b of the outer circle. It is preferred that the nose be vertical in order to lock in the visual orientation of the stimulus and the appearance of a face. For continuity in spatial frequency, the horizontal diameter of the nose may be substantially equal to the diameter of the eyes and/or of the thickness 17 of the outer circle. Preferably, the upper and lower points of the nose are spaced along the vertical diameter 6b from the concave inner edge of the arcs at a distance 30 which is substantially the thickness 17 of the outer circle. In similar fashion to the other elements of the stimulus, the shape, size and/or thickness of the nose may be varied so long as it is centered vertically and horizontally.

For the following description, the dimensions provided are preferable and provided as an illustration. However, the skilled person may vary these within a range as set out above while remaining within the acceptable test protocol. A non-limiting example of a testing protocol follows: The visual angle of the DH face and features are calculated at the horizontally displaced location of the face relative to the child and shown to the child at a distance of 40 cm. The diameter of the face measured at the outer side thereof is 12 cm, subtending 16.1 deg at 40 cm The features of the face and the spaces are approximately 1.25 cm in width. The average visual angle of the features is 1.67 deg (100.2 min arc or 2 log MAR) equivalent to 0.3 c/d in spatial frequency.

The channel spatial frequency of the DH face stimulus is 0.8 c/deg when calculated with the formula from Majaj et al' p. 811) (Majaj N J, Pelli D G, Kurshan P, Palomares M. "The role of spatial frequency channels in letter identification." Vision Research 2002; 42:1165-1184.) That is, the 5 strokes in the 16 deg DH face result in 0.8 c/deg channel SF. Both the feature frequency of 0.3 c/deg and the channel frequency of 0.8 c/deg are below the peak (maximum) spatial frequency of the CSF for square-wave gratings in normal adults. CS for stimuli created with square-wave edges is relatively constant for spatial frequencies lower than peak contrast sensitivity. Square wave CS is unlike CS for sine-wave gratings. Sine-wave CS is reduced for spatial frequencies below the peak CS. The DH stimulus contains square-wave like edges and the DH face features are near the peak contrast sensitivity for individuals with a range of visual acuity reduction. However, individuals with a visual acuity lower than the DH spatial frequency and channel frequency, i.e., 1.55 to 2.0 logMAR, may not have a measurable CS.

The DH test set used consisted of 16 cards, 15 printed with a face varying in contrast relative to the white card background and one card without a face stimulus. The Weber contrast of the stimuli ranges from 89% to 0.8% (0.05 to 2.1 $\log_{10}$ CS). Weber contrast was measured with a proprietary method. The difference in CS between the DH stimulus cards is 0.15 $\log_{10}$. Labels placed on two diagonally opposite corners of the rear of the card indicate the Weber contrast, CS, and $\log_{10}$ CS. Thus, there are no cues on the rear of the cards that give the location of the face stimulus on the card to the tester. The luminance of the white background of the DH cards was measured with a Konica Minolta LS-100 luminance meter as 2.1 $\log_{10}$ cd/m$^2$. A fluorescent lamp placed above and behind the child and parent holder illuminated the test cards. The test cards were held by the tester when s/he presents them to the child.

The test distance of 40 cm equals the horizontal length of the test card, which aids in the administration of the test. The tester measured the test distance with the card length before the test and as needed during the test.

The test procedure is similar to that recommended for clinical testing of grating visual acuity with Teller Acuity Cards® (In the field, TAC is considered as the standard and is a widely used test of visual acuity in pediatric vision research and clinical applications: Dobson V, Mayer D L, Candy R. Teller Acuity Cards II. Reference and Instruction 508 Manual. 2009). The DH cards are tested in sequence from highest to lowest contrast. But, unlike testing with the clinical TAC method, all DH cards are tested. The tester assesses the participant's responses for cards at suprathreshold contrast, usually presenting each only once or twice. The DH cards around contrast threshold (as determined below) are tested several times. Children's responses are defined as a fixation shift to one side of the card, searching the card and then fixating one side, or pointing to one side.

As in the recommended TAC test procedure, the tester is unaware of the location of the face and remains unaware until s/he determines whether the child detected the face. Only then the tester checks the location of the face on the card. If s/he is uncertain whether the participant detected the face on a specific card, the card is set aside and retested after higher contrast faces are detected successfully. The lowest contrast DH face that the child detected is then defined as their contrast threshold. Two testers tested all participants in this study. Both the order of the test and tester identity were block-randomized before each appointment. For example, for participant 1, tester A was the first tester and tester B the second tester; for participant 2, tester B was the first tester and tester A the second tester. The tests were completed in a single session in separate examination rooms. Participants were tested binocularly. The second tester was unaware of the first tester's test results.

Visual acuity was tested as part of the participant's clinical examination. Binocular acuity was measured to make VA measures comparable with DH CS thresholds. The participants wore their glasses for visual acuity and DH testing. The type of visual acuity test depended upon the participant's ability to respond, and the most advanced method was used for each patient. Line letter acuities were tested in 17 participants. Single optotypes (letters or symbols such as Lea [Goodlite, Elgin, Ill., USA] or Patti Pics [Precision Vision, Woodstock, Ill., USA] were tested with 10 participants who either named or matched the optotypes. Grating acuity was tested with the clinical TAC procedure in 16 participants.

Participants and diagnoses. Participants were recruited from those patients scheduled for an examination at the New England College of Optometry's clinic, New England Eye Low Vision Clinic at the Perkins School for the Blind. Inclusion criteria were: age between birth and age 18 years, and visual acuity better than 2 log MAR, if known. Recruited patients included both previously examined and new patients. Patients were not included or excluded based on their diagnosis. Patients with developmental disabilities were not excluded.

43 patients completed the study. The mean/median age of the participants was 6.9/6 years (SD 4.52, range 2 to 18 years). Mean binocular acuity was 0.68 log MAR (SD 0.43).

The participants' primary cause of visual impairment was divided into two categories, ocular disorder or cerebral/cortical visual impairment (CVI). Supplementary Material S1 provides details on the determination of ocular disorders and CVI diagnoses. Supplementary Table S2 provides ocular diagnostic information for each participant as well as neurological, genetic, syndromic, and systemic abnormalities, DH log contrast sensitivity (DH log 10 CS), and visual acuity (log MAR) with an indication of visual acuity test type.

Of the 43 participants, 23 had an ocular disorder with no evidence of CVI. Twenty (20) participants were diagnosed with CVI. Five (5) of the participants with CVI also had a significant ocular disorder: optic atrophy, optic atrophy and history of retinal hemorrhages; optic nerve and chiasmal hypoplasia; optic nerve hypoplasia; retinopathy of prematurity. However, visual function deficits (visual acuity, visual fields) associated with these ocular disorders did not explain their CVI (see Supplementary Material S1). Many participants had significant neurological or systemic disorders. Of the 43 study participants, 25% (11) had cerebral palsy, and 21% (9) had a seizure disorder. Cerebral palsy and seizure disorders were more frequent in participants with CVI (cerebral palsy in 10, seizures in 8) than in those with ocular/ocular motor disorder.

Results

Feasibility of DH CS test: All 43 participants were successfully tested for binocular DH log 10 CS by two testers. The total test time was approximately 2-3 minutes. A few participants required more time, especially if a break was needed.

It was predicted that participants with acuity below the DH spatial frequency or the channel spatial frequency (>1.55 to 2.0 logMAR) would not have measurable CS. Nevertheless, all participants had measurable CS. Three participants with reduced visual acuity at about the DH feature and channel spatial frequency (logMAR 1.51, 1.55, 1.55, respectively) had measurable CS (mean $\log_{10}$ CS 1.13, 0.98, 0.38, respectively). Testing DH CS in clinical practice also reveals some patients with poor acuity who have surprisingly good DH CS.

Test-retest reliability of DH $\log_{10}$ CS. There was no difference between DH $\log_{10}$ CS on test 1 vs. test 2 (t=−0.51, df=42, p=0.61). The mean difference between tests was −0.017, and the 95% confidence interval (CI), defined as the mean plus/minus 1.96 times the SD, was −0.58 to 0.54 log 10.

Inter-tester reliability of DH $\log_{10}$ CS. Cohen's kappa for two raters (unweighted) was 0.238 (z=4.16, p<0.001). Kappa for the ocular group (n=23) was 0.274 (z=3.05, p<0.01) and for the CVI group (n=20) 0.176 (z=2.19, p<0.05). The difference between the mean DH log 10 CS measured by the two testers in all participants was not statistically significant (paired t-test, Tester 1 mean 1.611, Tester 2 mean 1.615, difference −0.003, SD 0.226; t=−0.101, df 42, p=0.46). The 95% CI was −0.44 to 0.45 $\log_{10}$. CS. The ICC of DH $\log_{10}$ CS between the two testers was 0.921 (p<0.001).

The high level of agreement between testers led us to use DH log 10 CS for subsequent data analyses.

Figure 3:
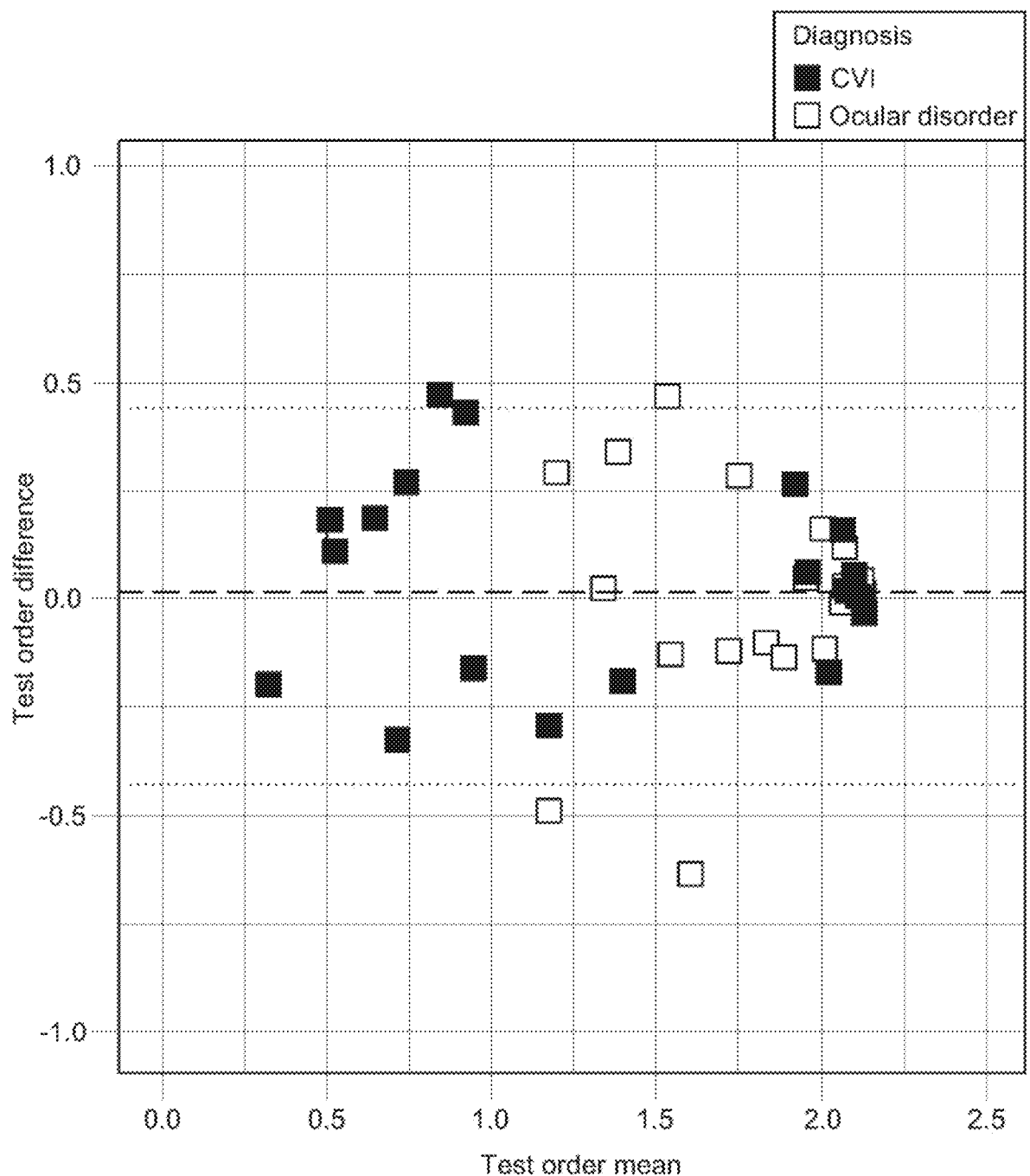
FIG. 3 shows a scatter diagram in which the filled squares represent DH log 10 CS scores for the CVI patients and the open squares for those with ocular disorder. The abscissa is the mean of the scores from the first and second test and the ordinate the difference between Test 1 and Test 2. The dashed line is the median difference between the first and second test, and the dotted lines the limits of the 95% confidence interval on the difference. Note that DH $\log_{10}$ CS scores were lower for those with CVI.

Bland-Altman analyses of test order and tester identity. FIGS. 3 and 4 show the Bland-Altman graphical analysis of test order and tester identity. The median difference shown in FIG. 3 is consistent with the previously stated observation of no significant difference between DH log 10 CS on test 1 vs. test 2. The Bland-Altman analysis depicted in FIG. 4 also agrees with the inferential test of inter-tester reliability.

Age at test. The mean DH $\log_{10}$ CS for all participants did not correlate significantly with age at test (Pearson r=0.243, p=0.12). Visual acuity (logMAR) did not correlate significantly with age at test (Pearson r=−0.025, p=0.87).

DH $\log_{10}$ CS and diagnosis. Using a Welch two-sample t-test, the means of DH $\log_{10}$ CS for the CVI vs. ocular disorder groups were different (t=−2.75, df=26.38, p=0.011). The 95% confidence of the difference ranged from −0.79 to −0.11. The mean DH $\log_{10}$ CS was 1.37 for the CVI group and 1.82 for the ocular disorder group.

Correlation between DH log 10 CS and visual acuity. FIG. 5 shows the mean CS from the two DH tests with an individual participant versus the individual's visual acuity; Pearson's r was −0.65 (p<0.01). To evaluate the robustness of the correlation and protect against high-leverage points, we used the bootstrap (Davison, A C, Hinkley, D V. *Bootstrap Methods and Their Applications*. Cambridge University Press, Cambridge. 1997; Efron B, Tibshirani R J. *An introduction to the bootstrap*. CRC press. 1994.) to calculate a 95% confidence interval on r. The range of the confidence interval for r was −0.80 to −0.44.

Linear mixed-model of DH log 10 CS. To evaluate the ability of the independent variables to predict mean DH log 10 CS, we used a linear mixed-effect model. The model was calculated with the R software environment and the nlme package (R Core Team. R: A language and environment for statistical computing. (*Foundation for Statistical Computing*, Vienna, Austria. 2019. URL: https://www.R-516 project.org; Pinheiro J, Bates D, DebRoy S, Sarkar D, R Core Team. nlme: Linear and Nonlinear Mixed Effects Models. R package version 3.1-141. 2019. URL: https://CRAN.R-519 project.org/package=nlme>). There are at least two benefits of linear mixed-effect models over repeated measures ANOVA. First, mixed-effect models have the benefit of assuming the variance of the residuals are normally distributed and not the data itself. Second, unlike repeated-measures ANOVA designs, mixed-models do not assume homoscedasticity of variance (i.e., that the variance within groups or independent variances is equal).

The full model used DH log 10 CS as a dependent variable with VA, Diagnosis, Age, and VA Test Type as fixed effects and Tester and Subject as random effects. In the full mixed-model VA (t=−2.91, p<0.01) and Test Type (t=−5.03, p<0.001) were significant. However, including both Age and Test Type in the model has the disadvantage that the VA Test Type correlates with both Age (0.53) and VA (−0.48). The selection VA Test Type was based on the participant's ability to perform the test, which correlated with age. Excluding the VA Test Type from the model, VA (t=−4.70, p<0.01) is significant while both Age (t=2.06, p=0.046) and Diagnosis (t=−1.79, p=0.081) are marginal.

One concern when modeling is over-fitting, which arises from including too many model parameters. To address the possibility of over-fitting, we used a backward stepwise procedure (James G, Witten D, Hastie T, Tibshirani R. *An introduction to statistical learning*. 521 New York: Springer; 2013) using the Akaike Information Criterion (AIC). Using AIC penalizes models that have more model parameters, and if a simpler model has a higher AIC, it is preferred over a more highly parameterized model. The full model had an AIC=32.4, while a simple model that includes only VA and Diagnosis an AIC=53.7. The increased AIC value shows the model with VA and Diagnosis is the most parsimonious model for the data. Under this reduced model VA (t=−4.67, p<0.001) is significant while Diagnosis remains marginal (t=−1.59, p=0.11).

Logistic regression to predict diagnosis from VA versus DH $\log_{10}$ CS. Logistic regression analysis uses a binary outcome variable and a continuous dependent variable to generate a model that can be used for prediction. We used logistic regression analysis as an exploratory tool to evaluate the predictive power of DH log 10 CS or VA for diagnosis. Under an Analysis of Deviance, (McCullagh P., Nelder J A. *Generalized Linear Models* (Vol. 37). CRC Press.; 1989) both logistic regression models were better than the null model (DH $\log_{10}$ CS: Deviance=−7.61, p=0.0058, VA: Deviance=−5.9879, p=0.014). Nagelkerke's $r^2$ (Nagelkerke N J. A note on a general definition of the coefficient of determination. 524 *Biometrika;* 1991:78:691-2) was used to compare the two models and mean DH $\log_{10}$ CS, explained 21.7% of the variance while VA explained 17.4% of the variance.

The new Double Happy Contrast Sensitivity Test was successful in assessing CS with a diverse pediatric population diagnosed with ocular disorders or CVI. Two testers successfully tested all 43 patients scheduled for an examination in a low vision clinic. Test time was rapid for most participants. Many participants had significant neurological or systemic disorders. Our success in testing this diverse pediatric clinical population may be because we did not recruit participants with very poor visual acuity (>2.0 log MAR). Also, we tested participants binocularly because clinical experience shows monocular testing is more difficult. DH testing was successful across the age range, 2-18 years. In our clinical experience, infants younger than 2 years also can be tested successfully with the DH test.

This study is the first to examine the inter-tester reliability of a test of CS in children with visual deficits. The Cohen kappa reliability statistics indicated only fair agreement between testers. However, the intraclass correlation coefficient (ICC) was significant. The average difference in DH $\log_{10}$ CS between the two testers was near zero, with the confidence interval of the difference at −0.44 to 0.45 log 10.

A previous study of adults found high DH $\log_{10}$ CS test-retest differences (Gerger K, Marcheva N, Kran B, Deng L, Mayer D L American Academy of Optometry, 2014, program #145113). Visually normal adults (39) were tested in two sessions in two conditions, with their habitual correction and with their visual acuity reduced optically. The 95% CI for DH $\log_{10}$ CS was −0.61 to 0.39 in the habitual correction condition and −0.44 to 0.43 in the optically reduced vision condition. Along with the results from our child participants, these results from adults suggest that DH CS has relatively high test-retest variability. That is, high variability may be a more general property of the DH CS test and not necessarily the result of the young age of participants or their visual impairments or other disabilities.

It was predicted that participants with acuity below the DH spatial frequency or the channel spatial frequency (>1.55 to 2.0 logMAR) would not have measurable CS. Nevertheless, all participants, including three with very reduced visual acuity, had measurable CS. Lower spatial frequencies than the nominal and channel spatial frequency are present in the DH stimulus and could provide a cue to its detection in participants with poor visual acuity. Adults that were tested reported using a part of the face, such as a portion of the circumference or the mouth, to detect its right or left location rather than the whole face at threshold. In half the conditions, the adults' acuity was not reduced. Thus, even subjects with good visual acuity may use very low spatial frequencies to detect the DH face at threshold.

In the present study, DH $\log_{10}$ CS was close to normal on average for the group with ocular disorders, while the average was reduced in the group with CVI. VEP studies found reduced CS in children with CVI who had no coexisting ocular disorder. Thus, children with CVI may be vulnerable for low CS regardless of their ocular status. VA was reduced both in those with CVI and in those with ocular disorders only. These results suggest CVI in young patients may show both low CS and low VA.

The correlation between DH CS and VA ($r=-0.65$) in our study suggests the two measures of visual function are not independent. The strength of the correlation is consistent with about 42% of shared variance. Notably, in an extensive study by Kiser et al (Kiser A K, Mladenovich D, Eshraghi F, Bourdeau D, Dagnelie G. Reliability and 526 consistency of visual acuity and contrast sensitivity measures in advanced eye disease. 527 *Optom Vis Sci.* 2005; 82:946-54) in adults with advanced ocular disorders, the correlation between VA and CS was $r=-0.80$ with a shared variance of 64%; the higher correlation in the Kiser study may be due to the larger range of VA and CS.

Modeling of the results of our study found that the best predictor of the DH $\log_{10}$ CS was visual acuity. Consistent with the analyses of inter-tester reliability, tester identity was not a significant predictor. In the experimental design, the type of visual acuity test covaried with age, which favors using a simpler model for predicting DH 1 $\log_{10}$ CS that does not include age or visual acuity test type. The regression analyses demonstrate that the most parsimonious model is one that includes VA and diagnosis. FIG. 5 shows the negative correlation between VA and DH $\log_{10}$ CS and clustering of the data for CVI vs. ocular disorder patients (filled and open symbols). The modeling and the correlation shown in FIG. 5 together show that the DH CS test provides additional information to the clinician beyond VA to guide diagnosis of CVI. The exploratory logistic regression modeling of diagnosis with DH CS and VA provides some modest support for this claim. However, neither test is a particularly powerful predictor, as shown by the relatively low percentage of the variance explained by the two logistic regression models.

The DH test has advantages over previous tests of CS developed for young children. It uses a 2-alternative forced-choice procedure and clinical method based on the TAC grating acuity test. The DH test is objective and relatively unbiased because the tester is unaware of DH stimulus location until s/he can judge if the participant detected the stimulus. This is in contrast to Hiding Heidi (HH) (Chen & Mohamed, 2003; Elgohary, Abuelela & Eldin, 2017) and Mr. Happy CS test (Fisher S, Orel-Bixler D, Bailey I. Mr. Happy Contrast Sensitivity: A behavioral test for infants and children. *Optom Vis Sci.* 1995; 72:204) where the tester may have knowledge of the right or left position of the stimulus during testing.

The DH test has a wide range of $\log_{10}$ CS values, greater than 2 log units, 0.05 to 2.1. The interval between $\log_{10}$ CS for each stimulus is smaller than other pediatric tests of CS (0.15 in DH test vs. 0.30 in HH test and CCT (0.19 for Mr. Happy. Smaller intervals between stimulus levels can result in more accurate outcomes.

Figure 2A:
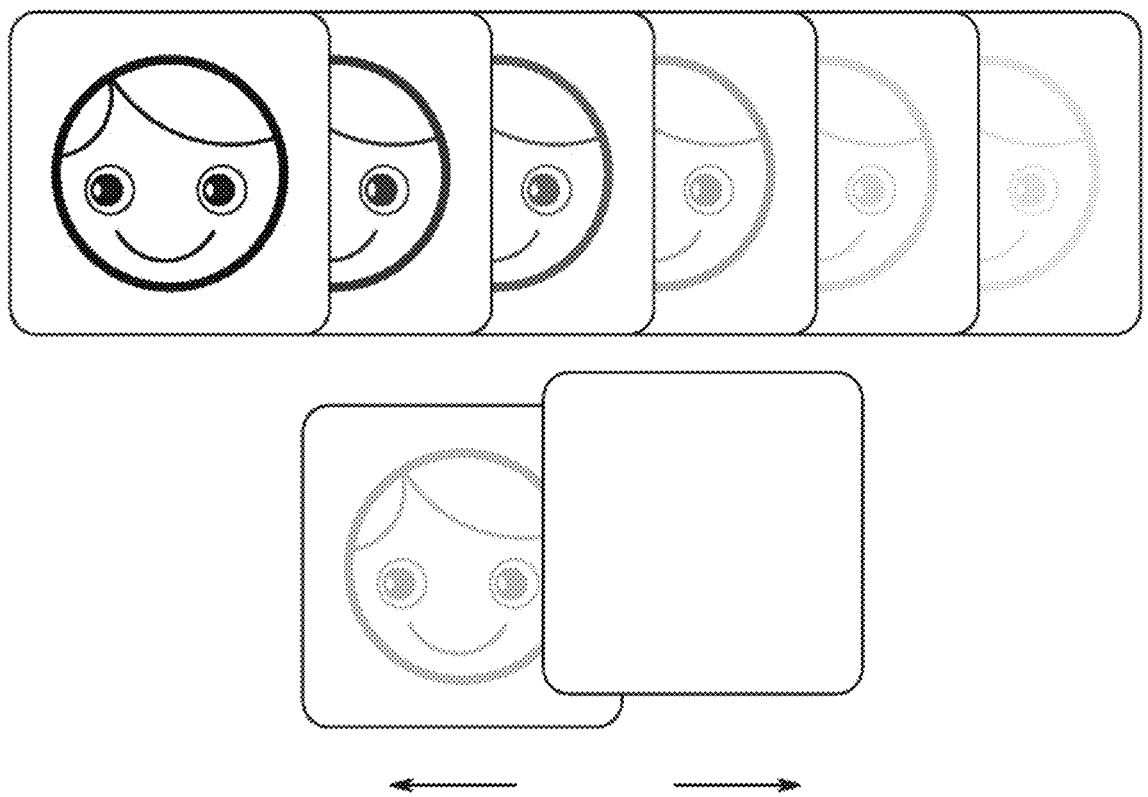
FIG. 2A refers to the prior art and shows a selection from a set of contrast cards FIG. 2B refers to the prior art and shows a selection from a different set of contrast cards.
Figure 2B:
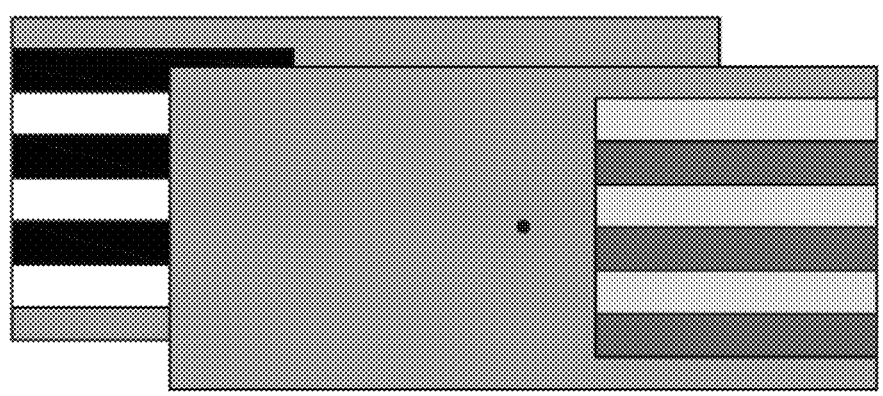

A face stimulus such as Double Happy may have greater interest for young children than a large grating as in the Ohio Contrast Cards (OCC) (FIG. 2B). Nevertheless, the testing protocol of the OCC has similar advantages to the DH test. The TAC testing method can be used with OCC because the large grating is printed on one side of the test cards. The OCC grating stimulus has square wave edges, chosen because CS for square-wave stimuli is high and relatively constant over a wide range of low spatial frequencies. The OCC uses a large range of CS and intervals of 0.15 $\log_{10}$ CS as in the DH set. The developers of the OCC test measured CS and a vision-related quality of life (QoL) measure in low vision students (Hopkins, Doherty & Brown, 2017). OCC CS was correlated with the QoL measure while Pelli-Robson CS was not, nor were two measures of visual acuity. A study of test-retest reliability of the OCC is in progress (A M Brown, personal communication, 2019).

Few published studies report test-retest reliability of CS in children and those that do show low reliability. CSF test-retest reliability for sine-wave gratings in chart format using a detection task (CSV-1000) was low, both with visually normal children age 5-12 years and adults (Kelly S A, Pang Y, Klemencic S. Reliability of the CSV-1000 in adults and children. *Optom Vis Sci.* 2012; 89:1172-81). In a study of test-retest reliability with sine-wave CSF in visually normal 3 month-old infants, Adams and colleagues found an average coefficient of reliability (COR) of $+/-0.49$ $\log_{10}$ CS across 4 spatial frequencies (Drover J R, Courage M L, Dalton S M, Adams R J. Accuracy of the contrast sensitivity 489 card test for infants: Retest variability and prediction of spatial resolution. *Optom Vis* 490 *Sci.* 2006; 83:228-232). (COR is equivalent to CI.) Test-retest reliability studies with other tests of behavioral CS in visually normal children and clinical populations are needed to judge whether behavioral tests of CS are more variable generally in children.

The following is a summary of the advantages/strengths (impact) of the new DH contrast test of the present application:

- Objective test because the face stimulus and card design enable a two-alternative forced-choice procedure where the tester can be unbiased
- CS thresholds can be measured because of large range of stimulus contrasts
- Successful and rapid assessment of threshold CS in pediatric patients, even those with developmental disabilities
- Parameters of between-tester reliability have been measured
- Between-tester reliability shows relatively high variability which was also shown for adults tested with the same stimuli; this may be a general property of behavioral tests of CS
- CS with this test may provide unique information on visual functioning independent of visual acuity CS with this test may be a sensitive indicator of neurological visual disorders such as cerebral/cortical visual impairment, which is the most prevalent cause of visual impairment in children

What is claimed is:

1. A contrast card comprising:

A visual stimulus in the form of a design, the design comprising:

an outer circle having a constant thickness,

A first arc segment within the outer circle which is symmetrical about the vertical diameter of the outer circle, and a second arc segment in opposing arrangement to the first arc segment and being identical in length and thickness to the first arc segment, the second arc segment being symmetrical about the vertical axis of the outer circle, the first and second arc segments being located on an imaginary circle residing within the outer circle and being concentric therewith, A first filled-in circle and a second filled-in circle being identical in diameter to the first filled-in circle, each residing adjacent to opposite ends of the horizontal diameter of the outer circle and each being equidistant from the center of the outer circle, A filled-in center element having a rotational center on the center of the outer circle, the center element being symmetrical about both the horizontal and vertical diameter of the outer circle, A horizontal axis of the card dividing the card into upper and lower symmetrical portions on either side of the horizontal axis;

A vertical axis of the card to dividing the card into left and right symmetrical portions on either side of the vertical axis;

The visual stimulus in the form of a design being located on the card so as to be symmetrical about the horizontal axis;

The visual stimulus in the form of a design being entirely located in one of the left and right symmetrical portions;

The visual stimulus in the form of a design being a variation of a smiling face that is an identical facial design whether viewed in a right-side up orientation of the card or in an upside-down orientation of the card;

The card further comprising a centrally located pinhole at the intersection of the horizontal axis and the vertical axis.

2. The contrast card of claim 1, wherein a thickness of each of the first and second arc segments is substantially the same as the thickness of the outer circle.

3. The contrast card of claim 1, wherein the length of the first and second arc segments are each from about 80 to 100 degrees of a circle.

4. The contrast card of claim 3, wherein the length of the first and second arc segments are each about 90 degrees of a circle.

5. The contrast card of claim 1, wherein each lateral ends of each of the first and second arc segments are rounded.

6. The contrast card of claim 1, wherein each of the first and second filled-in circle have a diameter which is substantially equal to the thickness of the outer circle.

7. The contrast card of claim 1, wherein the center element has a horizontal width which is substantially equal to the thickness of the outer circle.

8. The contrast card of claim 1, wherein the center element is a vertically oriented ellipse.

9. The contrast card of claim 2, wherein a radial distance between an inner concave edge of the outer circle and a convex outer edge of the first arc segment is substantially equal to the thickness of the outer circle.

10. The contrast card of claim 1, wherein the thickness of the outer circle is about 20-25%, of the outside radius of the outer circle.

11. The contrast card of claim 10, wherein the thickness of the outer circle is about 22% of the outside radius of the outer circle.

12. A set of contrast cards, comprising a plurality of identically sized rectangular contrast cards according to claim 1, wherein each of said cards comprises the design in a differing contrast from each of the other cards of the set.

* * * * *